United States Patent [19]
Smith

[11] 4,185,120
[45] Jan. 22, 1980

[54] TOPICAL TREATMENT OF FUNGAL OR YEAST INFECTIONS USING P-TOLYL DIIODOMETHYL SULFONE

[75] Inventor: Robert A. Smith, Lindenhurst, Ill.

[73] Assignee: Abbott Laboratories, North Chicago, Ill.

[21] Appl. No.: 947,328

[22] Filed: Oct. 2, 1978

[51] Int. Cl.² .............................................. A61K 31/10
[52] U.S. Cl. ..................................................... 424/337
[58] Field of Search ...................... 424/337; 260/607 A

[56] References Cited

U.S. PATENT DOCUMENTS

| | | | |
|---|---|---|---|
| 3,615,745 | 10/1971 | Crovetti | 424/337 X |
| 3,632,859 | 1/1972 | Crovetti | 260/607 A |
| 3,657,353 | 4/1972 | Crovetti et al. | 260/607 A |
| 3,663,623 | 5/1972 | Crovetti et al. | 260/607 A |

FOREIGN PATENT DOCUMENTS 50-46833  4/1975  Japan.

OTHER PUBLICATIONS

Chemical Abstracts 69:96242d (1968).

*Primary Examiner*—Leonard Schenkman
*Attorney, Agent, or Firm*—Paul D. Burgauer; Robert L. Niblack

[57] ABSTRACT

By incorporating p-tolyl diiodomethyl sulfone into a topically acceptable base, the growth of yeast or fungi on the skin of warm-blooded animals can be alleviated, reversed or eliminated.

7 Claims, No Drawings

TOPICAL TREATMENT OF FUNGAL OR YEAST INFECTIONS USING P-TOLYL DIIODOMETHYL SULFONE

DETAILED DESCRIPTION OF THE INVENTION

Many warm-blooded animals, including humans, are often plagued with skin infections caused by certain yeasts or fungi that seem to survive and grow on such skin. Infections of this type are difficult to treat as they often resist treatment with antibacterials and/or antibiotics.

Human fungal infections are normally separated into two classes: deep systemic mycoses, and superficial fungal infections. The most prevalent superficial infection is athlete's foot (dermatophytosis of the foot, tinea pedis). A third class of dermatophytic infection, or at least a somewhat different type, might be infections of the mucous membranes caused by trichomonal or monilial organisms. These types of vaginitis can be caused by a number of factors that predispose the tissue to infection by the monilial form, *Candida albicans*, such as prolonged use of tetracyclines, steroid therapy, diabetes and pregnancy.

Most of the common pathogens associated with tinea pedis as well as with vaginitis, *C. albicans*, have been shown to succumb to very small amounts of TDS by in vitro studies. The present invention is therefore directed to alleviating skin infections caused by the more commonly recognized skin pathogens.

It has been found that p-tolyl diiodomethyl sulfone (hereinafter referred to as TDS) possesses all the necessary characteristics to combat such infections and afflictions. The present invention is therefore directed to the method of treating fungal or yeast infections on the skin of a warm-blooded animals which comprises topically applying to the skin area so afflicted an antifungally effective amount of TDS in a pharmaceutically acceptable carrier suitable for topical administration. The term "skin" herein is intended to include epidermic as well as mucous membrane tissue.

TDS is a known material which is preferably prepared by iodinating the corresponding tolyl sulfonylacetic acid. This can be done by the methods described in U.S. Pat. Nos. 3,657,353 or 3,663,623. The purified material is then homogenously distributed in a suitable pharmaceutical vehicle designed for topical application, e.g., into a solution, lotion, cream, ointment, powder or aerosol. For practical topical administration, these dosage forms usually contain between 0.5 and 5.0% by weight of the active ingredient. A preferred range for the present invention is 0.5 to 2.0% by weight of TDS.

In order to show the activity and use of the present invention, reference is made to the following examples which, however, are not intended to limit the invention in any way. All percentages or parts given in these examples are by weight.

EXAMPLE 1

In order to establish the minimum inhibitory concentration of TDS, the following comparison study was carried out with dermatophyte powders, using five frequently encountered dermatophytic fungi and a common yeast in the test. The fungal mixture consisted of *Trychophyton rubrum* and *mentagrophytes*, *Microsporum canis* and *audouinii* and *Epidermophyton floccosum*. The yeast tested was *Candida albicans*. The minimum concentration needed to completely stop the growth of these microorganisms are shown below for the finely divided pure powders of the active materials.

|  | Mixtures of Fungi | *C. albicans* |
| --- | --- | --- |
| Ca undecylenate | 10 ppm | >10 ppm |
| Tolnaftate | 0.078 ppm | >10 ppm |
| TDS | 0.078 ppm | 1.3 ppm |

When formulated dermatophyte powders were tested against the same microorganisms, the fungi and yeast MIC figures for TDS were 12 ppm and 50 ppm, respectively; for Ca undecylenate the values were 100 ppm and 500 ppm while for Tolnaftate, 3 ppm and > 200 ppm were obtained.

EXAMPLE 2

In order to show the specificity of the TDS of this invention, comparison studies were carried out with compounds closely related to TDS. The organisms used in Example 1 were tested and the MIC values were established individually for sulfones: A=p-tolyl iodomethyl, B=p-tolyl dichloromethyl and C=p-tolyl dibromomethyl. The results are shown below:

|  | TDS | A | B | C |
| --- | --- | --- | --- | --- |
| *T. rubrum* | 0.6 | >10 | >10 | >10 |
| *T. mentagophytes* | 0.6 | >10 | >10 | >10 |
| *M. canis* | <0.01 | 0.3 | 10 | 10 |
| *M. audouinii* | 0.6 | >10 | >10 | >10 |
| *E. floccosum* | 0.6 | >10 | >10 | >10. |
| *C. albicans* | 1.3 | >10 | >10 | >10 |

The above tests were carried out by the two-fold agar dilution plate method whereby the plates were streaked with swabs of fungal spore suspensions calibrated at 650 mm on a spetrophotometer. The plates were incubated at 30 degrees C. for seven days.

EXAMPLE 3

The procedure and microorganisms of Example 1 were used in this comparison test which was carried out in formulated powders containing 2% of TDS in talcum powder. The MIC values obtained were as follows:

|  | Fungi Mixture | *C. albicans* |
| --- | --- | --- |
| TDS | 12 ppm | 50 ppm |
| Tolnaftate | 3 ppm | >200 ppm |
| Desenex | 100 ppm | 800 ppm |

As will be seen from the above studies, the activity of TDS is far superior to that of currently used, topical antifungal compounds and greatly superior to the activity of the closest analogs of TDS. The antifungal activity of pure TDS is about 6–13 times greater than that of its analogs or currently used antifugal powders; its activity is only surpassed in diluted (formulated powder) form by that of 2-naphthyl-N-methyl-N-(3-tolyl)thionocarbamate (tolnaftate) which, however, has no economically useable antiyeast activity. In fact, no antifungal drug currently in broad use has an anti-yeast activity comparable to that of TDS.

The TDS of the present invention can be incorporated into a topical dosage form by simply combining it homogeneously with talcum powder in a concentration of 1–5%. If desired, moisture absorbers, adhesive agents, perfumes and opacifying agents may be added. A typical formula contains 60% of talcum, 22% of kaolin, 16% of bentonite and 2% of TDS.

Solid dosage forms can also be applied by means of a dressing, gauze or other cellulosic material can be soaked in a solution of TDS such as an ethanol solution. The solvent is then evaporated, leaving the dry material on the fabric which is then used as a dressing for the afflicted skin area.

A topical solution can easily and simply be made by combining TDS at a concentration of 1–2% in ethanol. If propanol or isopropanol is the desired vehicle, a concentratio of only 1% TDS can be used because of the lower solubility of TDS in these alcohols.

Topical creams can be prepared in the usual fashion, whereby TDS is combined, at a concentration of 0.5–5.0%, with primary and secondary emulsifiers, thickeners, emollients, oleaginous material, humectants, preservatives and water containing, if desired, a stabilizer and/or a buffer. Similarly, lotions can be made by combining TDS with the ingredients used in the above solution but containing also one or more preservatives and stabilizers.

Ointments are made with the ingredients listed above for creams and combined in the fashion known to those skilled in the art. Petrolatum is ordinarily used as the oleaginous base which may be combined with lanolin.

For more sophisticated formulations, the new antiyeast/antifungal drug can be incorporated into an aerosol. A suitable aerosol is made by combining a 1–2% alcoholic solution of TDS with one or more propellants. Without the propellant, the solution is most advantageously placed in a rigid or semirigid spray bottle from which the solution is atomized through a suitable orifice by squeezing the semirigid container or through a pump device.

Compared to its toxicity, miniscule amounts of TDS are used in accordance with the present invention: in view of the oral $LD_{50}$ of 10 g/kg, the topical use represents an extremely high therapeutic index. Also, no allergic sensitization is observed on human skin following a patch test using TDS in a concentration 40 times greater than the concentration used, for instance, in the commercial adhesives used by paper hangers. Additionally, a 2% (weight/volume) suspension of TDS administered topically to female albino guinea pigs once daily for 5 days does not elicit a photosensitivity reaction in the test animals (modified test of Vinson; J. Soc. Cosmetic Chemists 17; 123 ff of 1966).

I claim:

1. The method of treating fungal or yeast infections on the skin of a warm-blooded animal comprising applying topically to the skin area so afflicted an antifungally effective amount of p-tolyl diiodomethyl sulfone in a pharmaceutically acceptable carrier suitable for topical administration.

2. The process of claim 1 wherein said carrier is an ointment base.

3. The process of claim 1 wherein said carrier is talcum powder.

4. The process of claim 1 wherein said carrier is an alcohol with 2–3 carbons.

5. The process of claim 4 wherein said alcohol is ethanol.

6. The process of claim 4 wherein said alcohol is isopropanol.

7. A pharmaceutical composition for inhibiting the growth of fungi and yeast on the skin of a warm-blooded animal comprising a topically administerable carrier containing 0.5–5.0% by weight of p-tolyl diiodomethyl sulfone; said composition being in the form of an ointment.

* * * * *